United States Patent [19]

Smigel

[11] Patent Number: 5,041,280

[45] Date of Patent: * Aug. 20, 1991

[54] TOOTHPASTE COMPOSITION FOR STAIN REMOVAL

[75] Inventor: Irwin E. Smigel, New York, N.Y.

[73] Assignee: Epilady USA, Inc., Culver City, Calif.

[*] Notice: The portion of the term of this patent subsequent to Sep. 20, 2000 has been disclaimed.

[21] Appl. No.: 103,533

[22] Filed: Oct. 1, 1987

[51] Int. Cl.$^5$ .................... A61K 7/18; A61K 7/20; A61K 7/16

[52] U.S. Cl. ......................... 424/52; 424/53; 424/54; 424/56; 424/57; 424/49

[58] Field of Search .................. 424/53, 57, 52, 54, 424/56, 49

[56] References Cited

U.S. PATENT DOCUMENTS

| | | | |
|---|---|---|---|
| 4,358,437 | 11/1982 | Duke | 424/52 |
| 4,405,599 | 9/1983 | Smigel | 424/53 |
| 4,431,630 | 2/1984 | Morton | 424/52 |
| 4,603,045 | 7/1986 | Smigel | 424/57 |

FOREIGN PATENT DOCUMENTS 1209319  10/1970  United Kingdom .

OTHER PUBLICATIONS

*The Condensed Chemical Dictionary,* 8th ed., Revised by Gessner G. Hawley, Van Nostrand Reinhold Co., N.Y., 1971, p. 27.

*Primary Examiner*—F. T. Moezie
*Attorney, Agent, or Firm*—Darby & Darby

[57] ABSTRACT

A toothpaste composition having the following ingredients, by weight:

| | |
|---|---|
| Dicalcium Phosphate dihydrate: | From 1.0% to 50% |
| Calcium Carbonate | From 1.0% to 50% |
| Sodium Bicarbonate | From 1.0% to 50% |
| Magnesium Carbonate | From 1.0% to 25% |
| Sorbitol 70% | From 1.0% to 50% |
| Corn Starch | From 0.5% to 10% |
| Cellulose Gum | From 0.5% to 5.0% |
| Calcium Peroxide | From 0.5% to 5% |
| Lathanol LAL (Sodium Lauryl Sulfoacetate) | From 0.1% to 5% |
| Aluminum Hydroxide | From 0.01 to 1% |
| Saccharinate (Sodium Salt) | From 0.05% to 2% |
| Flavoring material | From 0.05% to 2% |
| Alkylparaben | From 0.05% to 1.0% |
| Sodium monofluorophosphate | From 0.70% to 0.80% |
| Titanium Dioxide | From 0.1% to 10% |
| Deionized Water | From 10% to 50% |

12 Claims, No Drawings

TOOTHPASTE COMPOSITION FOR STAIN REMOVAL

FIELD OF THE INVENTION

The invention relates to a toothpaste composition adapted not only for cleaning natural teeth, but composite filling material as well and which contains substances for preventing tooth decay.

BACKGROUND

In filling cavities from which dental caries have been removed, it has become an increasing practice to employ composite filling material which is similar in color to that of natural tooth material.

Such composite filling material is generally composed of a resinous substance which is polymerized in situ and which provides a hard bearing surface which has the natural appearance of a normal tooth.

Unfortunately, the composite filling material has inherent porosity and is relatively easily stained.

In a normal mouth, a salivary protein pellicle envelopes the tooth and is subject to plaque accumulation. Oral hygiene dictates the removal of the plaque accumulation in order to prevent decay of the tooth structure as well as serious diseases of the gums.

In my earlier U.S. Pat. Nos. 4,405,599 and 4,603,045, I disclosed a toothpaste composition which is adapted for cleaning natural teeth and composite filling material as well.

In these earlier compositions, an ingredient thereof was sodium perborate. According to recent investigations and developments it has become desirable to provide a suitable alternative for this ingredient. There is also a mandatory requirement for corresponding labeling of products containing the same.

SUMMARY OF THE INVENTION

An object of the invention is to provide a toothpaste which is adapted for cleaning natural teeth as well as bonded composite filling material which contains substances for preventing tooth decay.

A further object of the invention is to provide a toothpaste which is specifically addressed to the removal of stain from composite filling material as well as from the tooth itself which contains substances for preventing tooth decay.

Another object of the invention is to provide a toothpaste composition which will be effective to remove the protein pellicles which normally envelope the teeth as well as plaque accumulation and which contains substances for preventing tooth decay.

Another object of the invention is to provide improvements in the compositions in my earlier patents and specifically to provide a composition which avoids the use of sodium perborate.

In order to satisfy the above and further objects of the invention, there is provided a toothpaste according to the invention consisting essentially of the following ingredients in percent, by weight:

| | |
|---|---|
| dicalcium phosphate combined with a carbonate or bicarbonate of a metal defined below; | 1.0–50% |
| a humectant selected from the group consisting of sorbitol, glycerine, propylene glycol, polyethylene glycol or polypropylene glycol having a molecular weight of 200 to 1000 and mixtures thereof; | 1.0 to 50% |
| thickening agent; | 1.0 to 15% |
| oxidizing agent having the formula $X_nY_m$ wherein: X is sodium, potassium, calcium, magnesium, zinc, lithium or aluminum n is an integer equal to 1, 2, or 3 Y is a percarbonate persulfate perphosphate or peroxide; and m is an integer equal to 1, 2 or 3; | 0.5 to 5% |
| a detergent having the formula $R_m-[X]_n-Z^-Y^+$ wherein: R is a radical having 6–18 carbon atoms X is ethylene oxide, propylene oxide or mixtures thereof n is from 0 to 100 Z is a sulfate, sulfonate or hydrogen, and Y is sodium, potassium or triethanolamine when Z is a sulfate or sulfonate; | 0.1 to 5% |
| a pH control acid or base to confer a pH of between 3 and 10 for the composition; and a wetting agent to control viscosity in an amount to make up 100%. | |

The metal of the carbonate or bicarbonate which is combined with dicalcium phosphate can be sodium, potassium, calcium, magnesium, aluminum, zinc or lithium.

The oxidizing agent is calcium peroxide, zinc peroxide, sodium peroxide, sodium persulfate, sodium percarbonate or sodium perphosphate.

The thickening agent can be corn starch and a gelling agent, the gelling agent being cellulose gum which can be combined or completely substituted by other gelling agents of the polyssaccharide family such as guar gum, sodium carrigeenan, calcium carrigeenan, gum tragacanth, Karaya, or hydrated silica; or Xanathan gum, or Carbopol 940 or glycerides of starch and V-gum (magnesium aluminum silicate).

The detergent can be sodium lauryl sulfoacetate or sodium lauryl sulfate. The pH control substance ordinarily is a base preferably aluminum hydroxide. In the event acid control is necessary, an organic acid such as citric acid, propionic acid or a mild weak dilution of an inorganic mineral acid such as hydrochloric acid can be used in order to achieve a pH between 3 and 7. In lieu of aluminum hydroxide, other alkaline compounds such as sodium carbonate, potassium hydroxide or sodium hydroxide can be incorporated to achieve a pH between 7 and 10 as desired.

Normally, the wetting agent to control the viscosity of the composition will be deionized water, although this can be substituted or combined with sorbitol, glycerine, propylene glycol polyethylene glycol, or a copolymer of polypropylene and polyethylene glycol ranging in molecular weight from 200 to 1,000. In general, water can be substituted completely or combined with any polyhydroxyalcohol-glycol groups.

In accordance with the above, a toothpaste composition which will satisfy the objects of the invention can be composed as follows.

| | |
|---|---|
| Dicalcium Phosphate dihydrate: | From 1.0% to 50% |
| Calcium Carbonate | From 1.0% to 50% |
| Sodium Bicarbonate | From 1.0% to 50% |
| Magnesium Carbonate | From 1.0% to 25% |

-continued

| | |
|---|---|
| Sorbitol 70% | From 1.0% to 50% |
| Corn Starch | From 0.5% to 10% |
| Cellulose Gum | From 0.5% to 5.0% |
| Calcium Peroxide | From 0.5% to 5% |
| Lathanol LAL (Sodium Lauryl Sulfoacetate) | From 0.1% to 5% |
| Aluminum Hydroxide | From 0.01 to 1% |
| Saccharinate (Sodium Salt) | From 0.05% to 2% |
| Flavoring material | From 0.05% to 2% |
| Alkylparaben | From 0.05% to 1.0% |
| Sodium monofluorophosphate | From 0.70% to 0.80% |
| Titanium Dioxide | From 0.1% to 10% |
| Deionized Water | From 10% to 50% |

The flavoring material is preferably composed as follows by weight:

| | |
|---|---|
| Menthol crystals | 20% |
| Oil of spearmint NF | 20% |
| Terpeneless spearmint | 30% |
| Oil of peppermint | 20% |
| Oil of anise | 10% |

In the ingredients which have been incorporated into the toothpaste composition, there are active constituents present in a carefully balanced combination to achieve the objects of the invention. These consist of Dicalcium Phosphate, combined with Calcium Carbonate, Magnesium Carbonate, Sodium Bicarbonate; Sorbitol, Cornstarch, Cellulose Gum, Calcium Peroxide, and Lathanol LAL. The invention covers these ingredients as well as their obvious equivalents.

The dicalcium phosphate, calcium carbonate, sodium bicarbonate and magnesium carbonate are cleaning agents. Additionally, the sodium bicarbonate is an alkalizer.

The Sorbitol is a humectant.

The cornstarch and cellulose gum are thickening agents.

The calcium peroxide is an oxidizing agent.

The Lathanol is a detergent.

The Aluminum Hydroxide is a pH adjuster and is present in an amount to provide the composition with a substantially neutral pH.

The Saccharinate and flavoring material are present as taste ingredients and can be varied according to the desired taste to be provided for the composition.

The Alkylparaben is a preservative and includes any of the various alkylparaben compositions (such as methylparaben, propylparaben) capable of acting as preservatives.

The sodium monofluorophosphate is an active agent which is compatible in the overall composition and provides topical fluoride for inhibiting tooth decay.

The titanium dioxide is a whitening agent.

The deionized water is present in an amount to confer a suitable wetness for the composition in accordance to the desired viscosity of the composition.

DESCRIPTION OF PREFERRED EMBODIMENTS

One of the most important advances in dentistry in the past twenty-five years has been the development of the composite (tooth colored) restoration. This has revolutionized the profession from an esthetic concept. This coupled with the evolution of light activation with its capability of controlling setting time and the dentist's ability to etch the enamel of teeth and thus bond the composite material directly onto the tooth is known as bonding. Bonding enables the dentist to close spaces between teeth, repair chips in teeth, cover discolorations and reshape abnormally shaped teeth. This coupled with the imminent development of composites for chewing surfaces of posterior teeth is expected to make the composite filling material the overwhelming material of choice in dentistry. However, the composite material for all of its advantages is inherently porous and is subject to staining. There are two types of composite filling material:

A. The conventional material which is composed of 76% inorganic filler material, such as quartz or Barium glass and 24% Resin Matrix, such as BIS GMA which is the reactive product of BIS Phenol A and Glycidyl Methyl acrylic.

B. Microfill—composed of 35-55% inorganic filler—such as fumed silica and 45-65%- Resin Matrix, generally BIS GMA.

The present invention provides for a toothpaste composition which is capable of cleaning natural teeth as well as the composite filling material.

The invention provides a toothpaste composition which will satisfy the above and which has a specific balance of active ingredients to clean natural teeth as well as composite filling material. This composition consists of the following ingredients given in percent by weight.

| INGREDIENT | AMOUNT IN % |
|---|---|
| Dicalcium Phosphate | 7.5 |
| Calcium Carbonate | 5. |
| Sodium Bicarbonate | 5. |
| Magnesium Carbonate | 1.25 |
| Sorbitol 70% | 20 |
| Cornstarch | 1.3 |
| Cellulose Gum | 4.0 |
| Calcium Peroxide | 3.9 |
| Lathanol LAL (Sodium Lauryl Sulfoacetate) | 0.7 |
| Aluminum Hydroxide | 0.1 |
| Saccharinate (Sodium Salt) | 0.5 |
| Flavoring Material | 1 |
| Consisting of: | |
| Menthol crystals | 20% |
| Oil of Spearmint NF | 20% |
| Terpeneless Spearmint | 30% |
| Oil of Peppermint | 20% |
| Oil of Anise (imitation) | 10% |
| Methylparaben (Hydrobenzoic acid methyl ester) | 0.5 |
| Propylparaben (Hydroxybenzoic acid propylester) | 0.03 |
| Sodium Monofluorophosphate | 0.76 |
| Titanium Dioxide | 1.0 |
| Deionized Water (to make up 100%) | 47.46 |

The above composition had the paste-like texture of standard toothpaste and was found to be exceptionally effective in its ability to remove stains and plaque from normal teeth as well as composite filling material. The sodium monofluorophosphate is compatible with the remainder of the ingredients and is active to provide a topical fluoride composition on the teeth and the composite filling material to inhibit decay.

It has been found that in order to prepare the toothpaste composition and retain the activity of the sodium monofluorophosphate, the composition must be prepared as set forth in the following example.

EXAMPLE

The required amount of water was added to a Hobart mixer whose agitation means was activated.

The calcium peroxide and sodium bicarbonate were added to the water and agitation was continued for ten minutes.

The sorbitol, methylparaben (or propylparaben or mixture thereof), cornstarch and aluminum hydroxide were then added and agitation was continued for an additional ten minutes.

Thereafter, the dicalcium phosphate, calcium carbonate, magnesium carbonate and sodiumonofluorophosphate were added and agitation was continued for another ten minutes.

The titanium dioxide and saccharinate were then added and agitation was continued for at least half an hour.

Finally, the lathanol and the cellulose gum were added and agitation was continued until a homogeneous mass was obtained. Then the flavor was added and permitted to blend thoroughly in the mass of the toothpaste.

It was found that the homogeneous mass was of suitable paste-like composition for use as the toothpaste composition of the invention.

While the invention has been described in connection with specific embodiments thereof, it will become apparent to those skilled in the art that various equivalents may be used within the scope and spirit of the invention as defined by the attached claims.

What is claimed is:

1. A toothpaste composition consisting essentially of in percentage by weight;
   1.0 to 50% of dicalcium phosphate combined with a carbonate or bicarbonate of a metal selected from the group consisting of zinc, aluminum, magnesium, calcium, sodium, potassium, and lithium;
   1.0 to 50% of humectant selected from the group consisting of sorbitol, glycerine, propylene glycol, polyethylene glycol, polypropylene glycol and mixtures thereof;
   1-15% of a thickening agent;
   0.5-5% of an oxidizing agent having the formula $[X]_n [Y]_m$ wherein X s selected from the group consisting of sodium, potassium, calcium, magnesium, zinc, aluminum, and lithium, Y is selected from the group consisting of percarbonate, persulfate, perphosphate, and peroxide, n is an integer of 1,2 or 3 and m is an integer of 1,2, or 3:
   0.1 to 5% of a detergent of the formula $R-[A]_q-Z^-B^+$ wherein R is a hydrocarbon radical containing 6-18 carbon atoms;
   A is selected from a group consisting of ethylene oxide, propylene oxide, and combinations thereof;
   q is an integer from 0 to 100;
   Z is selected from the group consisting of sulfate, sulfonate and hydrogen; and
   B is selected from the group consisting of sodium, potassium and triethanolamine but only when Z is a sulfate or sulfonate;
   a pH control agent to confer a pH to the composition between 3 and 10; and
   water to make 100% for the composition.

2. The composition of claim 1 further comprising a preservative.

3. The composition of claim 2 wherein the preservative alkyl paraben contained in an amount of 0.05-1.0%.

4. The composition of claim 1 wherein the humectant is a copolymer of polypropylene glycol and polyethylene glycol having a molecular weight of 200-1000.

5. The composition of claim 1 wherein said dicalcium phosphate is combined with a carbonate or bicarbonate of a metal selected from the group consisting of calcium, magnesium and combinations thereof.

6. The composition of claim 1 wherein said oxidizing agent is selected from the group consisting of calcium peroxide, zinc peroxide, sodium peroxide, sodium persulfate, sodium percarbonate and sodium perphosphate.

7. The composition of claim 1 wherein said detergent is selected from the group consisting of sodium lauryl sulfate and sodium lauryl sulfoacetate.

8. The composition of claim 1 further comprising taste ingredients.

9. The composition of claim 8 wherein said to ingredients comprises a sweetening agent in the amount of 0.05-2% and a flavoring agent in the amount of 0.05-2%.

10. The composition of claim 1 wherein said pH control agent is aluminum hydroxide and the pH is between 7 and 10.

11. The composition of claim 1 wherein said thickening agent is a polysaccharide gum.

12. The composition of claim 11 wherein said polysaccharide gum is cellulose gum.

* * * * *